(12) United States Patent
Shan et al.

(10) Patent No.: US 11,243,111 B2
(45) Date of Patent: Feb. 8, 2022

(54) INTEGRATED PHYSIOLOGICAL SIGNAL DETECTION SENSOR

(71) Applicants: Keeson Technology Corporation Limited, Zhejiang (CN); ZHEJIANG YANGTZE DELTA REGION INSTITUTE OF TSINGHUA UNIVERSITY, Zhejiang (CN)

(72) Inventors: Huafeng Shan, Zhejiang (CN); Jiadong Wang, Zhejiang (CN); Kaimin Cao, Zhejiang (CN); Hongwen Li, Zhejiang (CN); Yuan Yu, Zhejiang (CN)

(73) Assignees: Keeson Technology Corporation Limited, Jiaxing (CN); ZHEJIANG YANGTZE DELTA REGION INSTITUTE OF TSINGHUA UNIVERSITY, Jiaxing (CN)

(*) Notice: Subject to any disclaimer, the term of this patent is extended or adjusted under 35 U.S.C. 154(b) by 0 days.

(21) Appl. No.: 16/967,414

(22) PCT Filed: Aug. 1, 2018

(86) PCT No.: PCT/CN2018/097938
§ 371 (c)(1),
(2) Date: Aug. 5, 2020

(87) PCT Pub. No.: WO2019/153666
PCT Pub. Date: Aug. 15, 2019

(65) Prior Publication Data
US 2021/0215533 A1    Jul. 15, 2021

(30) Foreign Application Priority Data
Feb. 6, 2018    (CN) .......................... 201810119651.0

(51) Int. Cl.
*G01H 11/08*    (2006.01)

(52) U.S. Cl.
CPC ........ *G01H 11/08* (2013.01); *A61B 2562/182* (2013.01)

(58) Field of Classification Search
CPC ........................ G01H 11/08; A61B 2562/182
See application file for complete search history.

(56) References Cited

U.S. PATENT DOCUMENTS

| | | |
|---|---|---|
| 6,263,734 B1 | 7/2001 | Fujii et al. |
| 7,690,058 B1 | 4/2010 | Dwyer et al. |
| | (Continued) | |

FOREIGN PATENT DOCUMENTS

| | | |
|---|---|---|
| CN | 203275498 U | 11/2013 |
| CN | 106500826 A | 3/2017 |
| | (Continued) | |

OTHER PUBLICATIONS

Extended European Search Report of Counterpart European Patent Application No. 18904518.0 dated Sep. 23, 2021.

*Primary Examiner* — Herbert K Roberts
*Assistant Examiner* — John M Royston

(57) ABSTRACT

Disclosed is an integrated physiological signal detection sensor, comprising a movable housing member, a fixed housing member, and a sensing unit circuit board. The movable housing member and the fixed housing member are connected to form an internal space therebetween. The sensing unit circuit board is fixedly installed on the fixed housing member within the space. A piezoelectric film is attached to the sensing unit circuit board. A hollowed-out region surrounds the periphery of the piezoelectric film. A protrusion is provided on the movable housing member at a position corresponding to the piezoelectric film. The sensor of the present invention has advantages of simplified sensor installation, improved signal integrity, and simplified wire routing of an electromagnetic shield layer, thereby eliminat- (Continued)

ing errors caused by sensor installation and improving the accuracy of data detection.

6 Claims, 2 Drawing Sheets

(56) References Cited

U.S. PATENT DOCUMENTS

| | | | |
|---|---|---|---|
| 2001/0047686 A1* | 12/2001 | Baba | G01P 1/023 |
| | | | 73/504.12 |
| 2006/0214202 A1* | 9/2006 | Zorich | G01L 9/0055 |
| | | | 257/294 |
| 2008/0024158 A1* | 1/2008 | Turner | G01R 1/0408 |
| | | | 324/764.01 |
| 2010/0229303 A1 | 9/2010 | Goldsmith | |
| 2014/0352068 A1 | 12/2014 | Xu | |
| 2015/0351671 A1 | 12/2015 | Vanslyke et al. | |
| 2018/0092556 A1* | 4/2018 | Ishiguro | A61B 5/6833 |
| 2018/0325384 A1* | 11/2018 | Agarwal | A61B 5/113 |

FOREIGN PATENT DOCUMENTS

| | | |
|---|---|---|
| CN | 206847790 U | 1/2018 |
| CN | 206852599 U | 1/2018 |
| WO | 1998041818 A1 | 9/1998 |
| WO | 2015039373 A1 | 3/2015 |

\* cited by examiner

INTEGRATED PHYSIOLOGICAL SIGNAL DETECTION SENSOR

FIELD OF THE INVENTION

The present disclosure relates to the technical field of micro-vibration sensor structure design, and in particular, to an integrated physiological signal detection sensor.

BACKGROUND OF THE INVENTION

The application principle of a piezoelectric film sensor is as follows. The piezoelectric film has characteristics such as being light, thin, soft and high in sensitivity and is very sensitive to dynamic stress, and thus it is used as a dynamic strain sensor, which is often applied in the field of physiological signal detection to convert physiologically weak vibration signals into piezoelectric signals so as to realize data collection of physiological characteristics. A relative movement of an upper cover and a lower cover of the sensor causes a fulcrum of the upper cover to press one end of a suspended beam support, so that the beam support bends downward. Since the beam support has a certain degree of hardness, uniform downward bending deformation of the beam support drives the piezoelectric film closely attached to the beam support to deform uniformly, so that the sensor can collect physiological parameters.

An existing piezoelectric film mainly has the following defects:

1. A sensor is connected to a signal processing circuit board via a wire or by direct welding, and thus data collection is influenced by radiation interference caused by external connection; and moreover, an introduction of installation errors results in inaccuracy of a signal detection result.

2. Installation of most existing sensors is exposed in air without any shielding measure, and thus it is hard to avoid electromagnetic interference in space and power frequency interference.

3. A conductive wire is required for connecting a shielding layer on a housing member of an existing sensor to a shielding ground signal point or a reference signal point of a circuit board, which results in complexity in an installation process; or the reference signal point of the sensor directly abuts against a shielding layer on a surface in a movement direction of a movable housing member via an flexible piece such as an ejector pin or a spring. The flexible piece is prone to introduce direct vibration errors which results in inaccuracy of a data detection result.

SUMMARY OF THE INVENTION

The objective of the present disclosure is to provide an integrated physiological signal detection sensor with respect to deficiencies in existing technologies. The sensor can not only simplify sensor installation and improve signal integrity but also simplify wire routing of an electromagnetic shield layer, thereby eliminating errors caused by sensor installation and improving the accuracy of data detection.

In order to achieve the above objective, the present disclosure adopts the following technical solution. An integrated physiological signal detection sensor is provided. The sensor includes a movable housing member, a fixed housing member, and a sensing unit circuit board. The movable housing member and the fixed housing member are connected to form an internal space therebetween; the sensing unit circuit board is fixedly installed on the fixed housing member within the space; a piezoelectric film is attached to the sensing unit circuit board, and a hollowed-out region surrounds the periphery of the piezoelectric film; and a protrusion is provided on the movable housing member at a position corresponding to the piezoelectric film.

Further, the sensing unit circuit board is fixedly installed on the fixed housing member via set screw columns.

Further, the movable housing member and the fixed housing member are provided respectively at opposite surfaces thereof with a shielding layer.

Further, a POGOPIN connector of the sensor is mounted on an edge of the sensing unit circuit board, and is in contact with the shielding layer of the movable housing member.

Further, the sensing unit circuit board and the fixed housing member are provided therebetween with a flexible pad.

Further, at least one piezoelectric film is attached to the sensing unit circuit board; each of piezoelectric films is surrounded by a hollowed-out region; and the movable housing member is provided at a position corresponding to each of piezoelectric films with at least one protrusion.

The present disclosure has the following advantages:

1. The movable housing member and the fixed housing member of the sensor in the present disclosure are sealed with a flexible rubber gasket, so that an upper housing member can return to an original position because of action of a silicone pad after a stress disappears; and moreover, the piezoelectric film and the fixed housing member are provided therebetween with a flexible pad, which may mitigate interference of external vibration, so that the sensor in the present disclosure can obtain better vibration signals.

2. The piezoelectric film of the sensor in the present disclosure is attached to the sensing unit circuit board and is surrounded by a hollowed-out region on the periphery thereof, which facilitates wire routing on the circuit board. In this way, after vibration signals are converted into charge output signals by the piezoelectric film, the signals can be transmitted to a signal processing circuit in a shortest route for performing filtration and amplification, so that processes, from collection of electrical signals to outputting of a processing result, are all performed on the same circuit board, which improves signal integrity and avoids installation errors caused by external connection of the sensor.

3. The movable housing member and the fixed housing member of the sensor in the present disclosure are both provided with a shielding layer, and the sensing circuit board is provided at an edge thereof with a POGOPIN connector which is configured to be in contact with an electrically conductive coating of the movable housing member laterally. In this way, the movable housing member is in communication with a reference potential of the circuit board; and meanwhile, an effect of a positive pressure applied on the movable housing member when a flexible contact piece is installed vertically on the movable housing member can be avoided.

BRIEF DESCRIPTION OF THE DRAWINGS

Preferred embodiments of the present disclosure will be illustrated in detail hereinafter in combination with the accompanying drawings to make the purpose, features, and advantages of the present disclosure clearer.

Reference signs and components related in the accompanying drawings are as follows:

1. movable housing member, 2. fixed housing member, 3. sensing unit circuit board, 4. flexible rubber gasket, 5. set screw column, 6. flexible pad, 7. POGOPIN connector, 8. connector for external communication and power supply, 11. protrusion, 31. piezoelectric film, and 32. hollowed-out region.

DETAILED DESCRIPTION OF THE EMBODIMENTS

A structure of the sensor according to the present disclosure will be described in detail through two specific embodiments, so as to make the structure of the sensor more easily understandable and clearer.

Figure 1:
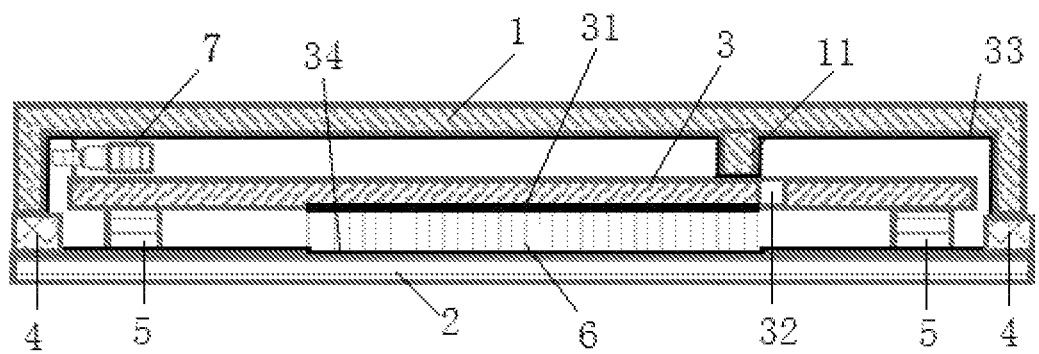
FIG. 1 schematically shows a structure of an integrated physiological signal detection sensor according to the present disclosure.

As shown in FIG. 1, an entire structure of an integrated physiological signal detection sensor according to the present disclosure includes a movable housing member 1, a fixed housing member 2 and a sensing unit circuit board 3. The movable housing member 1 and the fixed housing member 2 are connected by a flexible rubber gasket 4 to form an internal space therebetween. In actual use, in order to achieve an optimal shielding effect, a flexible electrically conductive material is usually selected to connect the movable housing member 1 and the fixed housing member 2. Most preferably, a flexible rubber pad, such as a silicone pad, is selected. The flexible rubber pad has resilience. When an external surface of the movable housing member 1 receives a force in a vertical direction, the silicone pad is extruded, so that a relative movement with micro displacement is caused between the movable housing member 1 and the fixed housing member 2; and when the force received by the movable housing member 1 disappears, the movable housing member can return to an original position because of action of the silicone pad, so as to ensure stability of the structure of the sensor.

As shown in FIG. 1, the sensing unit circuit board 3 is located in the internal space jointly formed by the movable housing member 1 and the fixed housing member 2, and is fixedly mounted on the fixed housing member 2. Benefits of such mounting are as follows: a fixed connection between the sensing unit circuit board 3 and the fixed housing member 2 can reduce interference of environmental vibration; and moreover, in practice, a contact point can be disposed on the fixed housing member 2 to conduct a shielding layer 34 on the fixed housing member 2 with a reference terminal circuit on the sensing unit circuit board 3, so as to play a role of shielding interference. A piezoelectric film 31 is attached to a surface of the sensing unit circuit board 3. Depending on the actual application scenario, the piezoelectric film 31 may be attached to a surface of the sensing unit circuit board 3 close to the movable housing member 1, or the piezoelectric film 31 may be attached to a surface of the sensing unit circuit board 3 close to the fixed housing member 2. The movable housing member 1 is provided at a position corresponding to the piezoelectric film 31 with a protrusion 11. The protrusion is closely attached to the piezoelectric film 31, and vibration signals are transmitted to the piezoelectric film 31 via the protrusion 11 of the movable housing member 1.

Embodiment One

Figure 2:
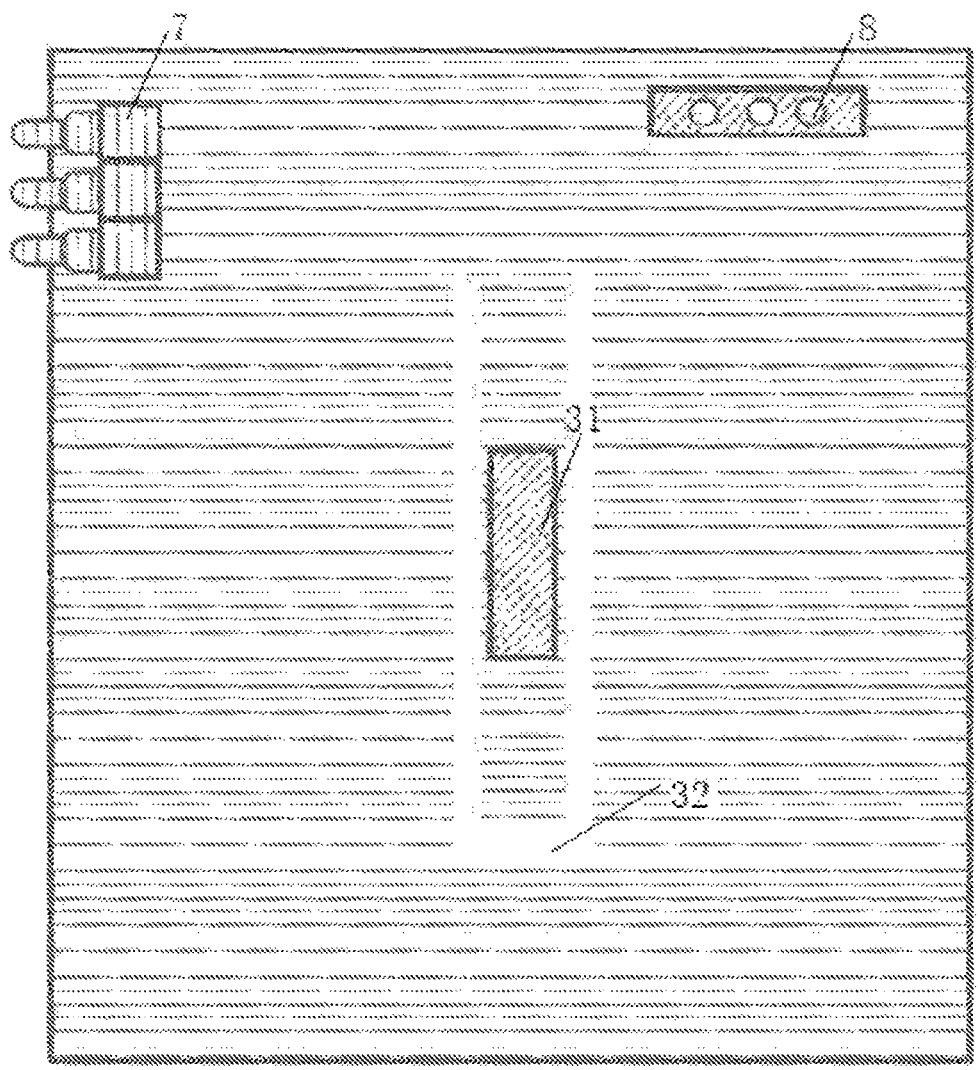
FIG. 2 schematically shows a planar view of a structure of a sensing unit circuit board according to Embodiment One of the present disclosure.

Embodiment One will be described in detail in combination with a view of a structure of a sensing unit circuit board schematically showed in FIG. 2. In the present embodiment, the sensing unit circuit board 3 is fixedly mounted on the fixed housing member 2 via set screw columns 5; a piezoelectric film 31 is attached to a surface of the sensing unit circuit board 3 close to the fixed housing member 2; and the piezoelectric film 31 and the fixed housing member 2 are provided therebetween with a flexible pad 6. The flexible pad 6 may mitigate vibration interference caused by action of an external pressure applied on the fixed housing member 2, so that the piezoelectric film 31 can obtain more accurate vibration signals.

In the present embodiment, the piezoelectric film 31 on the sensing unit circuit board 3 is provided with on the periphery of the piezoelectric film 31 with a rectangular hollowed-out region 32, so that a piezoelectric film region on the sensing unit circuit board 3 surrounded by the hollowed-out region may vibrate freely to form a suspended beam structure. Specifically, the rectangular hollowed-out region 32 has three hollowed sides, and one remaining non-hollowed side is used for wire routing. Vibration signals detected by the sensing unit circuit board 3 are converted into charge output signals by the piezoelectric film 31, and the signals are transmitted to a signal processing circuit in a shortest route for performing filtration and amplification. Amplified analog signals are changed into digital signals via AD conversion, and the digital signals are algorithm-processed by a processor. The arrangement of the hollowed-out region 32 enables simplified wire routing for the piezoelectric film 31 under the premise of ensuring accurate signal detection, so that entire processes, from collection of electrical signals generated by the piezoelectric film to outputting of a processing result, are all performed on the same circuit board, which improves signal integrity and avoids installation errors caused by external installation of the sensor. In order to further enhance a restraining effect of the sensor to radiation interference caused by external connection, a surface of the movable housing member 1 and a surface of the fixed housing member 2, in particular, a surface of the internal space, are respectively provided with a shielding layer (which is formed by performing electroplating to a surface of a housing member or by directly attaching a material such as a conductive fabric). When the sensor is in operation, it is required that the movable housing member 1 and the fixed housing member 2 be both in communication with a reference potential of the sensing unit circuit board 3. Since the sensing unit circuit board 3 is fixedly mounted on the fixed housing member, in order to enable conduction between the fixed housing member 2 and the reference potential on the sensing unit circuit board 3 so as to shield interference from an external magnetic field, the fixed housing member 2 may be provided thereon with a contact point to achieve communication with the reference potential. It can be seen from FIG. 2 that a POGOPIN connector 7 of the sensor in the present disclosure is mounted on an edge of the sensing unit circuit board 3, and is in contact with the shielding layer 33 of the movable housing member 1, so as to achieve communication between the movable housing member 1 and the reference potential of the sensing unit circuit board 3. Meanwhile, interference resulted from a positive pressure applied on the movable housing member 1 by a flexible contact piece when the flexible contact piece is installed vertically on the movable housing member 1, which affects signal detection, can also be avoided. The shielding layer may be formed by performing an electroplating metallization treatment to a housing member or by making a simple arrangement with a material such as a conductive fabric, and the purpose of arranging the shielding layer is to enhance an effect of resistance to radiation interference by the sensing unit circuit board and protect the piezoelectric film 31 which is relatively sensitive.

Embodiment Two

Figure 3:
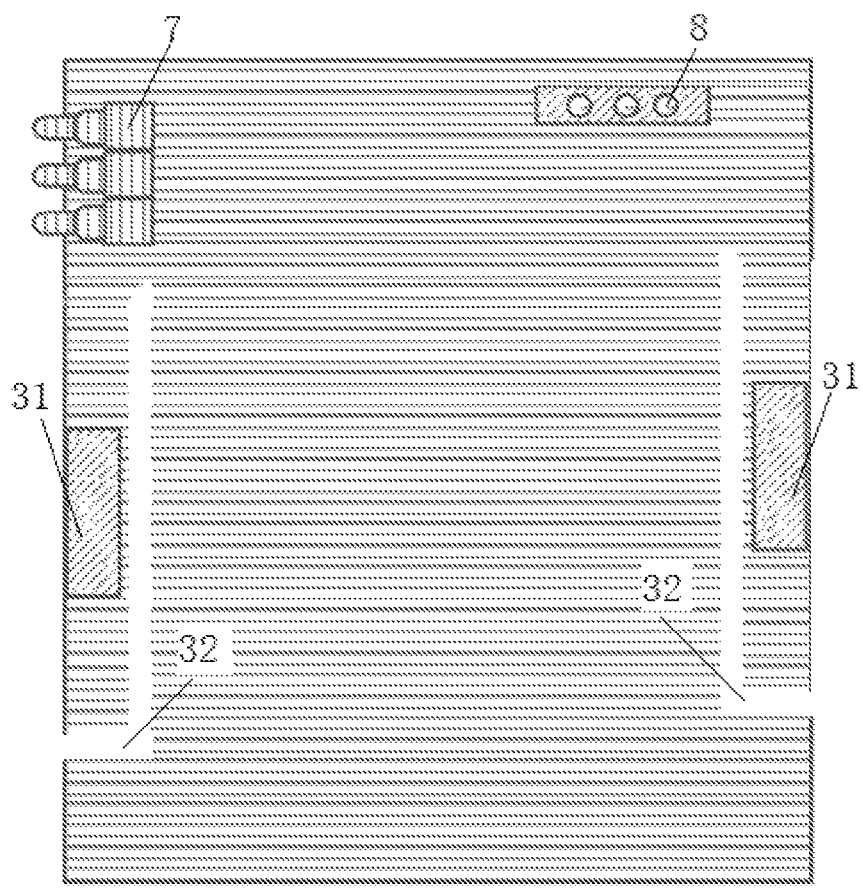
FIG. 3 schematically shows a planar view of a structure of a sensing unit circuit board according to Embodiment Two of the present disclosure.

Embodiment Two will be described in detail in combination with a view of a structure of a sensing unit circuit board schematically showed in FIG. 3. In the present embodiment, the sensing unit circuit board 3 is fixedly mounted on the fixed housing member 2 via set screw columns 5; two piezoelectric films 31 are attached to a surface of the sensing unit circuit board 3 close to the movable housing member 1; and each of the piezoelectric films 31 and the fixed housing member 2 are provided therebetween with a flexible pad 6. The flexible pad 6 may mitigate vibration interference caused by action of an external pressure applied to the fixed housing member 2, so that the piezoelectric films 31 can obtain more accurate vibration signals.

In the present embodiment, each of the two piezoelectric films 31 on the sensing unit circuit board 3 is attached to an edge of the sensing unit circuit board 3, and the periphery of each of the two piezoelectric films 31 are provided with a right-angle hollowed-out region 32, so that a piezoelectric film region on the sensing unit circuit board 3 surrounded by the hollowed-out region may vibrate freely to form a suspended beam structure. Specifically, each of right-angle hollowed-out region 32 surrounds one of the piezoelectric films 31, and one remaining non-hollowed side is used for wire routing. Correspondingly, the movable housing member 1 is provided at each of positions corresponding to one of the two piezoelectric films 31 with a protrusion 11, and the movable housing member 1 may be provided at each of the positions corresponding to one of the piezoelectric films 31 with one or more protrusion. Vibration signals detected by the sensing unit circuit board 3 are converted into charge output signals by the piezoelectric film 31, and the signals are transmitted to a signal processing circuit in a shortest route for performing filtration and amplification. Amplified analog signals are changed into digital signals via AD conversion, and the digital signals are algorithm-processed by a processor. The arrangement of the hollowed-out regions 32 enables simplified wire routing for the piezoelectric films 31 under the premise of ensuring accurate signal detection, so that entire processes, from collection of electrical signals generated by the piezoelectric films to outputting of a processing result, are all performed on the same circuit board, which improves signal integrity and avoids installation errors caused by external installation of the sensor. In order to further enhance a restraining effect of the sensor to radiation interference caused by external connection, a surface of the movable housing member 1 and a surface of the fixed housing member 2, in particular, a surface of an enclosed internal space, are respectively provided with a shielding layer. When the sensor is in operation, it is required that the movable housing member 1 and the fixed housing member 2 be both in communication with a reference potential of the sensing unit circuit board 3. Since the sensing unit circuit board 3 is fixedly mounted on the fixed housing member, in order to enable conduction between the fixed housing member 2 and the reference potential on the sensing unit circuit board 3 so as to shield interference from an external magnetic field, the fixed housing member 2 may be provided thereon with a contact point to achieve communication with the reference potential. It can be seen from FIG. 3 that a POGOPIN connector 7 of the sensor in the present disclosure is mounted on an edge of the sensing unit circuit board 3, and is in contact with the shielding layer of the movable housing member, so as to achieve communication between the movable housing member 1 and the reference potential of the sensing unit circuit board 3. Meanwhile, interference resulted from a positive pressure applied on the movable housing member 1 by a flexible contact piece when the flexible contact piece is installed vertically on the movable housing member 1, which affects signal detection, can also be avoided. The shielding layer may be formed by performing an electroplating metallization treatment to a housing member or by making a simple arrangement with a material such as a conductive fabric, and the purpose of arranging the shielding layer is to enhance an effect of resistance to radiation interference by the sensing unit circuit board and protect the piezoelectric films 31 which are relatively sensitive.

The contents described above are only preferred embodiments of the present disclosure. It should be noted that several improvements and supplements may be made by those skilled in the art without departing from the present disclosure, and these improvements and supplements may be regarded as being within the protection scope of the present disclosure.

The invention claimed is:

1. An integrated physiological signal detection sensor, wherein the sensor comprises a movable housing member, a fixed housing member, and a sensing unit circuit board, wherein the movable housing member and the fixed housing member are connected to form an internal space therebetween; the sensing unit circuit board is fixedly installed on the fixed housing member within the space; a piezoelectric film is attached to the sensing unit circuit board, and a hollowed-out region surrounds the periphery of the piezoelectric film; and a protrusion is provided on the movable housing member at a position corresponding to the piezoelectric film;

the movable housing member and the fixed housing member are provided respectively at opposite surfaces thereof with a shielding layer; and
a POGOPIN connector of the sensor is mounted on an edge of the sensing unit circuit board, and is in contact with the shielding layer of the movable housing member.

2. The integrated physiological signal detection sensor according to claim 1, wherein the sensing unit circuit board is fixedly installed on the fixed housing member via set screw columns.

3. The integrated physiological signal detection sensor according to claim 1, wherein the sensing unit circuit board and the fixed housing member are provided therebetween with a flexible pad.

4. The integrated physiological signal detection sensor according to claim 1, wherein at least one piezoelectric film is attached to the sensing unit circuit board.

5. The integrated physiological signal detection sensor according to claim 4, wherein each piezoelectric film is surrounded by a hollowed-out region.

6. The integrated physiological signal detection sensor according to claim 4, wherein the movable housing member is provided at a position corresponding to each piezoelectric film with at least one protrusion.

* * * * *